United States Patent
Hayek (10) Patent No.: US 10,549,035 B2
(45) Date of Patent: Feb. 4, 2020

(54) SYSTEMS AND METHODS FOR INTRATHECAL DELIVERY OF A PHARMACEUTICAL AGENT

(71) Applicant: University Hospitals, Cleveland, OH (US)

(72) Inventor: Salim M. Hayek, Cleveland, OH (US)

(73) Assignee: UNIVERSITY HOSPITALS HEALTH SYSTEM, INC., Cleveland, OH (US)

( * ) Notice: Subject to any disclaimer, the term of this patent is extended or adjusted under 35 U.S.C. 154(b) by 580 days.

(21) Appl. No.: 15/114,953

(22) PCT Filed: Jan. 28, 2015

(86) PCT No.: PCT/US2015/013253
§ 371 (c)(1),
(2) Date: Jul. 28, 2016

(87) PCT Pub. No.: WO2015/116658
PCT Pub. Date: Aug. 6, 2015

(65) Prior Publication Data
US 2016/0346470 A1 Dec. 1, 2016

Related U.S. Application Data

(60) Provisional application No. 61/934,214, filed on Jan. 31, 2014.

(51) Int. Cl.
*A61M 5/172* (2006.01)
*A61K 9/00* (2006.01)
(Continued)

(52) U.S. Cl.
CPC ......... *A61M 5/1723* (2013.01); *A61K 9/0085* (2013.01); *A61K 31/445* (2013.01);
(Continued)

(58) Field of Classification Search
CPC ............ A61M 5/1723; A61M 5/14244; A61M 5/14276; A61M 2210/1003; A61M 2230/30
See application file for complete search history.

(56) References Cited

U.S. PATENT DOCUMENTS 5,119,832 A * 6/1992 Xavier ................. A61N 1/0551
600/373
5,662,689 A * 9/1997 Elsberry ............ A61N 1/36071
607/46
(Continued)

FOREIGN PATENT DOCUMENTS

WO WO 2004033036 A2 4/2004

OTHER PUBLICATIONS

Jose de A, Luciano P, Vicente V, Juan Marcos AS, Gustavo FC. Role of Catheter's Position for Final Results in Intrathecal Drug Delivery. Analysis Based on CSF Dynamics and Specific Drugs Profiles. Korean J Pain. 2013;26(4):336-46.*
(Continued)

*Primary Examiner* — Nathan R Price
*Assistant Examiner* — Melissa A Snyder
(74) *Attorney, Agent, or Firm* — Renner, Otto, Boisselle & Sklar, LLP (57) ABSTRACT

An intrathecal delivery system for a pharmaceutical includes a reservoir containing a volume of the pharmaceutical agent, and a pump configured to deliver a portion of the pharmaceutical agent contained in the reservoir. A controller is configured to receive biological cycle information pertaining to a biological cycle (e.g., cardiac cycle), and configured, based on the received biological cycle information, to control the pump to deliver the pharmaceutical agent into a patient's intrathecal space as a high-speed bolus at a time corresponding to a time determined based on Processing the biological cycle information. The high-speed bolus may be delivered at a rate of 10-100 μL per second. The timing of such delivery corresponds to a time within the biological cycle when cerebrospinal fluid flow is optimal for intrathecal delivery of the pharmaceutical agent. Conditions for which treatment is enhanced by the intrathecal delivery system
(Continued)

include refractory hypertension, spasticity and chronic pain management.

20 Claims, 5 Drawing Sheets (51) Int. Cl.
*A61K 31/445* (2006.01)
*A61K 31/485* (2006.01)
*A61M 5/142* (2006.01)
*A61M 25/00* (2006.01)

(52) U.S. Cl.
CPC ....... *A61K 31/485* (2013.01); *A61M 5/14276* (2013.01); *A61M 25/0068* (2013.01); *A61M 2005/1726* (2013.01); *A61M 2210/1003* (2013.01); *A61M 2230/30* (2013.01); *A61M 2230/42* (2013.01)

(56) References Cited

U.S. PATENT DOCUMENTS

| | | | |
|---|---|---|---|
| 5,899,927 A * | 5/1999 | Ecker | A61N 1/3702 600/486 |
| 7,917,208 B2 * | 3/2011 | Yomtov | A61M 5/14276 607/120 |
| 2004/0133184 A1 | 7/2004 | Hildebrand | |
| 2005/0148927 A1 * | 7/2005 | Ludin | A61M 5/14276 604/66 |
| 2007/0253994 A1 * | 11/2007 | Hildebrand | A61K 31/192 424/422 |
| 2008/0021503 A1 | 1/2008 | Whitehurst et al. | |
| 2010/0312084 A1 | 12/2010 | Radojicic | |
| 2012/0087869 A1 | 4/2012 | Thakker et al. | |

OTHER PUBLICATIONS

Martin BA, Reymond P, Novy J, Balédent O, Stergiopulos N. A coupled hydrodynamic model of the cardiovascular and cerebrospinal fluid system. Am J Physiol Heart Circ Physiol 2012; 302: H1492-509.*
C. Lundborg et al., High Intrathecal Bupivacaine for Severe Pain in the Head and Neck, Acta Anaesthesiol Scand, 2009; 53: 908-913.
Lennart Appelgren M.D.., PhD. et al., Continuous Intracisternal and High Cervical Intrathecal Bupivacaine Analgesia in Refractory Head and Neck Pain, American Society of Anestesiologists Inc, 1996; 84; 256-72.
International Search Report and Written Opinion for International Application No. PCT/US2015/013253, dated May 4, 2015.

* cited by examiner

SYSTEMS AND METHODS FOR INTRATHECAL DELIVERY OF A PHARMACEUTICAL AGENT

RELATED APPLICATION DATA

This application is a national phase of International Patent Application Serial No. PCT/US2015/013253, filed on Jan. 28, 2015 which claims priority to U.S. Provisional Patent Application Ser. No. 61/934,214, filed on Jan. 31, 2014, the contents if which is incorporated here by reference.

TECHNICAL FIELD OF THE INVENTION

The technology of the present disclosure relates generally to intrathecal delivery of a pharmaceutical agent, and more particularly to enhanced systems and methods for intrathecal delivery of a pharmaceutical agent by a high-speed bolus delivery timed relative to a biological cycle (e.g., the cardiac cycle).

BACKGROUND

In intrathecal delivery of a pharmaceutical agent, the pharmaceutical agent is administered adjacent to the spinal cord in what is referred to as the intrathecal space (which also is referred to as the subarachnoid space). The intrathecal space is filled with the cerebrospinal fluid (CSF), which bathes and protects the brain and spinal cord. In conventional intrathecal delivery systems, a patient may be implanted with a small pump containing the pharmaceutical agent. A catheter extends from the pump and into the intrathecal space at a desired location along the spinal cord depending on the precise condition being treated. The pump operates to deliver the pharmaceutical agent through the catheter and into the CSF within the intrathecal space.

Intrathecal delivery has advantages over oral medication for certain conditions. By administering the pharmaceutical agent intrathecally, the agent may be delivered directly to neural receptors of the spinal cord that control certain biological states. Common examples of intrathecal treatments include treatments for chronic pain relief and blood pressure regulation. By administering the pharmaceutical agent directly to spinal receptors associated with pain, or receptors that control blood pressure (or other suitable receptors for other conditions), such conditions can be treated more efficiently and at less dosages than oral medications for the same condition, which must be digested, absorbed, and travel through the bloodstream.

In conventional intrathecal delivery systems, pumps are controlled to administer the pharmaceutical agent in essentially a continuous and "slow" manner. In this context, a slow delivery tends to be infused at a rate of 0.2 to 0.5 ml/day and an optional patient-controlled bolus delivery of up to about 10 microliters (µL) per minute, which constitutes the approximate upper limit on the delivery rate in conventional intrathecal delivery systems. The result of such a slow and continuous delivery is to administer up to about 0.2-0.6 milliliters per day for a typical intrathecal delivery system.

Although intrathecal delivery of a pharmaceutical agent has certain advantages over oral medication, intrathecal delivery systems have experienced their own drawbacks. Certain significant drawbacks result from the nature of the flow of the CSF within the intrathecal space.

The nature of the flow of the CSF within the intrathecal space has been the subject of substantial study. It has been found that the CSF flow tends to oscillate back and forth in accordance with the cardiac cycle, with minimal if any net movement in a cycle. In particular, during the systole portion of the cardiac cycle, the CSF tends to flow away from the brain, and during the diastole portion of the cardiac cycle, the CSF tends to flow oppositely from systole and toward the brain. The result of this back-and-forth movement is that during a complete cardiac cycle, there is little overall movement of the CSF. There is a minute component of bulk flow of the CSF around the brain and spinal cord, but such bulk flow is negligible as compared to the oscillatory flow, the bulk flow accounting only for less than about 0.5% of the CSF flow.

To a lesser extent as compared to the cardiac cycle, CSF flow also is influenced by the respiratory cycle. During expiration, when the diaphragm is forcing air outward, the abdominal and thoracic pressures are increasing and tend to force the CSF flow toward the brain. Conversely, during inhalation, when the abdominal and thoracic pressures negatively are pulling air inward, CSF flow tends to be away from the brain. Although the influence of the respiratory cycle on CSF flow tends to be significantly less than that of the cardiac cycle, both cycles produce an oscillatory rather than bulk flow. As referenced above, the result of this back-and-forth movement is that during these cycles, there is little overall movement of the CSF, with any component of bulk flow being essentially negligible.

The predominance of the oscillatory nature of the CSF flow has ramifications for intrathecal delivery of a pharmaceutical agent. In particular, with the slow and continuous administering of conventional systems, there is only a slight distance of travel of the pharmaceutical agent from the catheter at the low rates of currently available intrathecal pumps. Accordingly, to ensure delivery of the pharmaceutical agent to the appropriate spinal receptors, the catheter placement must be precise and in close proximity to the target receptors. In addition, the build-up of pharmaceutical agent (particularly opiates) adjacent the catheter, due to the low travel distance, can lead to an adverse complication known as a "granuloma". A granuloma is a collection of immune cells that build up around the catheter as the catheter/medication is "perceived" by the immune system to be an unwanted foreign body. Granulomas interfere with the effective administering of the pharmaceutical agent and can grow in size to cause nerve damage. As referenced above, this appears to result from the pharmaceutical agent building up adjacent the catheter due to low travel distance caused by the oscillating CSF flow.

Accordingly, current systems for intrathecal delivery of a pharmaceutical agent have been shown to have significant drawbacks.

SUMMARY

In view of the above deficiencies of conventional systems for intrathecal delivery of a pharmaceutical agent, there is a need in the art for an improved intrathecal delivery system. The present invention overcomes the deficiencies of conventional systems by (1) administering the pharmaceutical agent intrathecally as a high-speed bolus rather than as a continuous flow at low rates to increase travel distance, and (2) timing the delivery of the bolus with a portion of a biological cycle, and particularly the cardiac cycle, so that a component of the oscillatory CSF flow further increases the travel distance of the pharmaceutical agent and in a direction toward target spinal receptors. In exemplary embodiments, the volume of each bolus being administered is 10-20 µL, and each bolus is administered at a delivery rate in the range of about 10-100 μL per second, or higher up to approximately 1 ml per second.

In accordance with such features, an aspect of the invention is an intrathecal delivery system for a pharmaceutical or biological agent. In exemplary embodiments, the intrathecal delivery system includes a reservoir containing a volume of the pharmaceutical agent, and a pump configured to deliver a portion of the pharmaceutical agent contained in the reservoir. A controller is configured to receive biological cycle information pertaining to a biological cycle (e.g., cardiac cycle), and is configured, based on the received biological cycle information, to control the pump to deliver the pharmaceutical agent into a patient's intrathecal space as a high-speed bolus at a time corresponding to a time determined based on the biological cycle information and the intrathecal catheter tip location. As referenced above, the high-speed bolus may be delivered at a rate of 10-100 μL per second or higher up to approximately 1 ml per second. The timing of such delivery corresponds to a time within the biological cycle when cerebrospinal fluid flow is optimal for intrathecal delivery of the pharmaceutical agent.

In exemplary embodiments, the intrathecal delivery system further includes a biological sensor that senses the biological cycle information and transmits the biological cycle information to the controller. The biological cycle may be at least the cardiac cycle, and further may include the respiratory cycle. The controller is configured to control the pump to deliver the portion of the pharmaceutical agent at a time corresponding to a portion of at least the cardiac cycle, and in exemplary embodiments additionally the respiratory cycle.

In exemplary embodiments, the intrathecal delivery system further includes a catheter in fluid communication with the pump, wherein the catheter has a catheter tip that is inserted into the patient's intrathecal space to administer the bolus of the pharmaceutical agent. The catheter tip may include an injector to control a flow rate of the high-speed bolus into the patient's intrathecal space.

Another aspect of the invention is a method of intrathecal delivery of a pharmaceutical agent into a patient's intrathecal space. In exemplary embodiments, the method of intrathecal delivery includes the steps of: placing a catheter at an intrathecal spine location selected for treating a present medical condition; setting a predetermined volume of a bolus dosage of the pharmaceutical agent; setting a predetermined high-speed flow rate for administering the bolus dosage of the pharmaceutical agent; monitoring a biological cycle; determining whether the biological cycle has reached a portion in which a cerebrospinal fluid (CSF) flow is optimal for intrathecal delivery of the pharmaceutical agent; and when the biological cycle has reached a portion in which the CSF flow is optimal for intrathecal delivery of the pharmaceutical agent, administering the bolus dosage of the pharmaceutical agent of the predetermined volume at the predetermined flow rate into the patient's intrathecal space.

The disclosed systems and methods may be employed for treatment of any conditions suitable for treatment by an intrathecal delivery system, including, for example, refractory hypertension and chronic pain (with or without spasticity). When treating refractory hypertension in particular, blood pressure may be monitored to determine whether the blood pressure has risen to a high blood pressure condition. When the blood pressure has risen to a high blood pressure condition, the intrathecal delivery system is triggered. In addition, the intrathecal delivery system may be controlled to perform a feed forward control operation to account for potential over-correction of the high blood pressure condition. The pharmaceutical agent may include bupivacaine for treating refractory hypertension. The pharmaceutical agent may include morphine, hydromorphone, bupivacaine or a compound like ziconotide for treating chronic pain.

Comparable systems and methods to those described above may be employed to deliver a pharmaceutical agent into other internal fluid-filled bodily spaces or cavities. Additional bodily cavities may include, for example, interstitial or venous cavities. A high speed bolus may be employed for delivery of a pharmaceutical agent into such bodily cavities, or any other suitable bodily cavities. In addition, to the extent fluid flow within such cavities is tied to or influenced by a biological cycle, the delivery of the pharmaceutical agent further may be timed in accordance with biological cycle information so as to enhance deliver of the pharmaceutical agent to a specific location within or adjacent to the bodily cavity or space.

These and further features will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the scope of the claims appended hereto.

Features that are described and/or illustrated with respect to one embodiment may be used in the same way or in a similar way in one or more other embodiments and/or in combination with or instead of the features of the other embodiments.

DETAILED DESCRIPTION OF EMBODIMENTS

Embodiments will now be described with reference to the drawings, wherein like reference numerals are used to refer to like elements throughout. It will be understood that the figures are not necessarily to scale.

Figure 1:
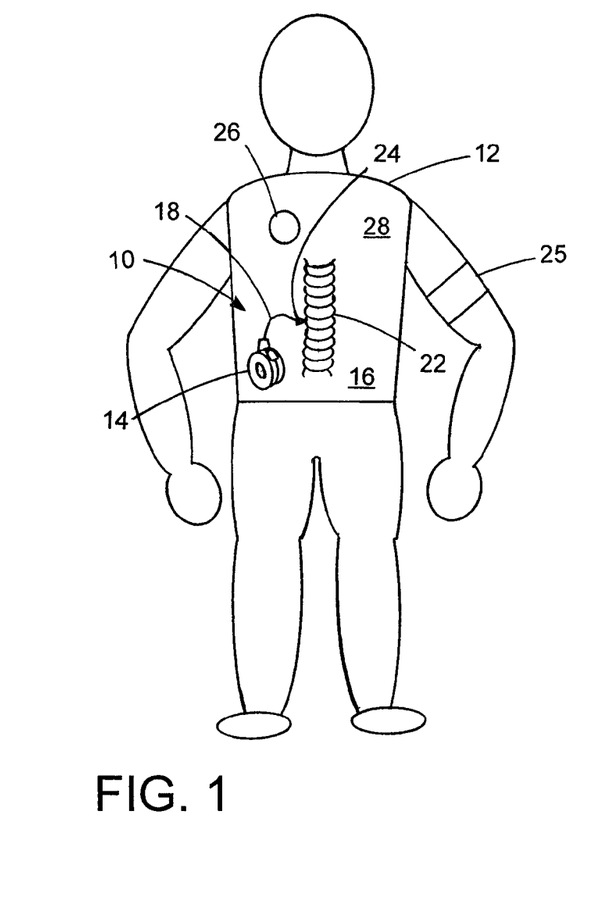
FIG. 1 is a schematic diagram depicting an exemplary system for intrathecal delivery of a pharmaceutical agent in accordance with embodiments of the present invention, with FIG. 1A being a closer view of a pump for use in the depicted intrathecal delivery system.
Figure 1A:
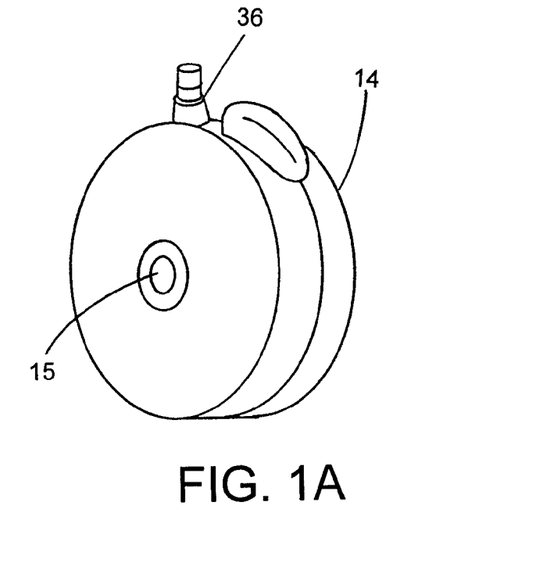

FIG. 1 is a schematic diagram depicting an exemplary system 10 for intrathecal delivery of a pharmaceutical agent to a patient 12, with FIG. 1A being a closer view of a pump system 14 for use in the depicted intrathecal delivery system 10. The pump system 14 contains and administers a pharmaceutical agent selected based upon a condition being treated. Although pump system configurations may vary, the example pump system in FIGS. 1/1A has a rounded housing configuration with a central port 15 for filling the pump system 14 with a pharmaceutical agent.

Generally, for patient convenience, it is desirable that the pump system 14 be as portable as practicable. Accordingly, in the example of FIG. 1, the pump system 14 is depicted as being implanted into the abdominal region 16 of the patient 12. Implantable pumps are know in the art and may be used in connection with intrathecal delivery of a pharmaceutical agent. External pump systems also may be employed. Portable external pumps, for example, may be worn on the body using a belt, pouch, or like support structure. In an in-patient hospital setting, in which patient travel and portability is less of an issue, non-portable external pump systems may be employed. Because patient freedom and convenience is a main concern, the pump system generally will be described in connection with an implantable pump system, although it will be appreciated that any suitable pump positioning relative to the patient may be employed depending upon the circumstances.

The intrathecal delivery system 10 further includes a catheter 18 that runs from the pump system 14 into the intrathecal space adjacent the spinal cord within the spine 22. The catheter 18 includes a catheter tip 24 that provides an injection point of the pharmaceutical agent into the intrathecal space. As explained in further detail below, the pump system 14 operates to administer a dosage of the pharmaceutical agent through the catheter 18, and into the intrathecal space via the catheter tip 24.

The system 10 further may include a biological sensor 26 for detecting biological cycle information. In exemplary embodiments, the biological cycle is the cardiac cycle. The biological sensor 26 relatedly may detect blood pressure as it cycles between systolic and diastolic pressure in correspondence with the cardiac cycle. The biological cycle additionally may be the respiratory cycle of inhalation and expiration.

In the example of FIG. 1, the biological sensor 26 is depicted as being implanted in the thoracic region 28 of the patient 12. Implantable sensors are known in the art for monitoring biological cycles such the cardiac, blood pressure, and respiratory cycles, and the thoracic region has proven to be a suitable location for implanting such sensors. It will be appreciated, however, that other suitable biological sensor configurations may be employed. For example, the biological sensor 26 may be incorporated into the pump system 14 rather than being implanted as a separate element. In other examples, external sensors, such as skin-placed electrodes, may be employed. When blood pressure is being detected, a blood pressure cuff 25 and associated blood pressure monitoring device may be employed. Generally, therefore, the configuration and positioning of the biological sensor may be varied as suitable to particular circumstances and medical conditions being treated.

Figure 2:
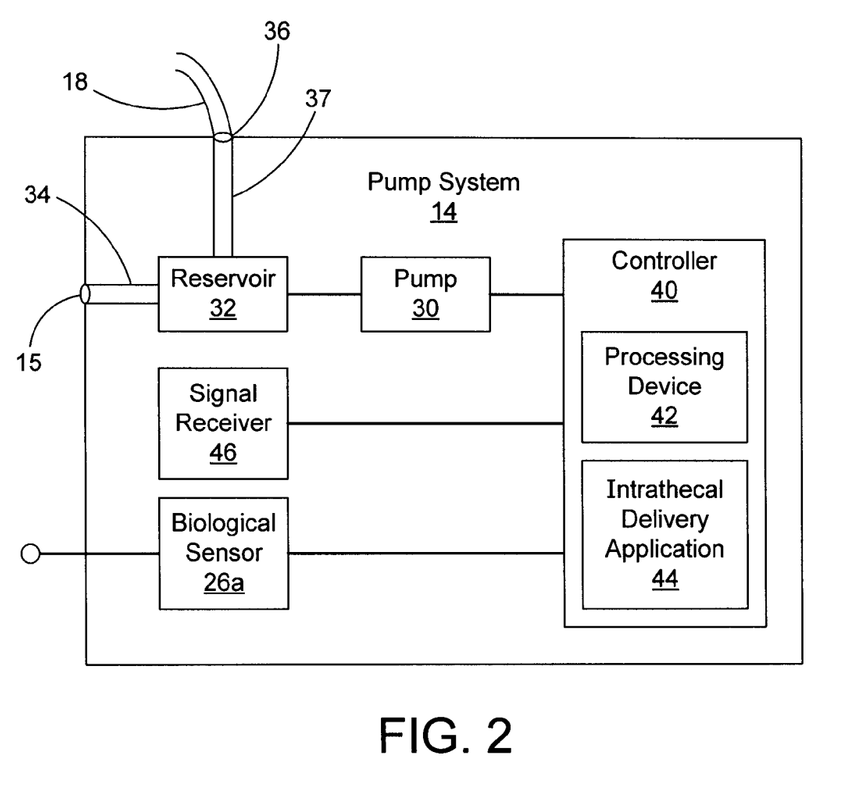
FIG. 2 is a block diagram depicting operative portions of an exemplary pump system for use as part of the intrathecal delivery system of FIG. 1.

FIG. 2 is a block diagram depicting operative portions of the exemplary pump system 14 for use as part of the intrathecal delivery system 10 of FIG. 1. As referenced above, for patient convenience it is desirable that the pump system 14 be as portable as practicable. Accordingly, the various mechanical components for administering a bolus of a pharmaceutical agent, as well as the related electronic control components, are depicted in FIG. 2 as being integrated into a single pump system 14. It will be appreciated that various elements, and particularly the electronic control components, may be configured as separate elements, and various configurations of component positioning and location relative to other components may be employed.

Referring to FIG. 2, the pump system 14 includes a pump 30 in communication with a reservoir 32. The reservoir 32 is configured as an internal containment vessel for containing a source volume of the pharmaceutical agent. Typical pump systems for intrathecal delivery have a capacity of up to about 30 milliliters of a pharmaceutical agent. The reservoir is fillable as needed from the port 15 referenced above via a first fluid pathway 34. The pump is configured to deliver a portion of the pharmaceutical agent contained in the reservoir in bolus dosages, as further explained below. The pump system also has a catheter port 36 that serves as a connection point for the catheter 18. The catheter is connected to the reservoir via a second fluid pathway 37. The pump system further may have any suitable valves and seals (not shown), or the like to regulate flow as between the first fluid pathway 34 from the filling port and the second fluid pathway 37 to the catheter port. In operation, the pump 30 operates to pump the pharmaceutical agent from the reservoir 32 into the catheter 18 via the fluid pathway 37 and port 36. The pharmaceutical agent is then forced up by the pump action through the catheter (including the catheter tip) and into the intrathecal space.

For control of the operation of the pump 30 to administer the pharmaceutical agent, the pump system 14 may include a controller 40 with one or more processing devices 42 that executes an intrathecal delivery application 44. The intrathecal delivery application 44 may be embodied as computer program code stored on a non-transitory, computer readable medium, such as a computer memory device. The computer readable medium may be any suitable memory device, but the memory device should be of a nature that can be sized for use in an implantable pump, such as for example a flash memory.

Figure 3:
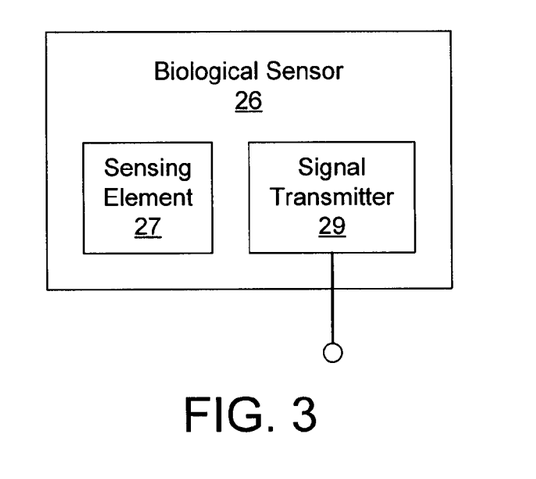
FIG. 3 is a block diagram depicting operative portions of an exemplary biological sensor for use as part of the intrathecal delivery system of FIG. 1.

The pump system 14 further may include a signal receiver 46 that is in electronic signal communication with the biological sensor 26 that senses biological cycle information. Referring briefly to FIG. 3, FIG. 3 is a block diagram depicting operative portions of an exemplary biological sensor 26 depicted as part of the intrathecal delivery system of FIG. 1. The biological sensor 26 may include a sensing element 27 and a signal transmitter 29. The sensing element 27 may obtain information pertaining to a biological cycle (e.g., the cardiac, blood pressure, and/or respiratory cycles). Such sensed information may then be transmitted by the signal transmitter 29 to the controller 40 via the signal receiver 46 of the pump system 14. Preferably, the signal transmitter 29 and signal receiver 46 constitute a wireless interface by which biological cycle information is transmitted by wireless signal to the pump system 14, which in turn is used by the controller 40 as part of the control of administering the pharmaceutical agent. Referring again to FIG. 2, in an alternative embodiment, the pump system 14 may include a biological sensor 26a in embodiments in which the biological sensor is integrated into the pump system 14 itself. In such case, the biological sensor transmits the biological cycle information directly to the controller 40 via an internal electronic pathway.

Figure 4:
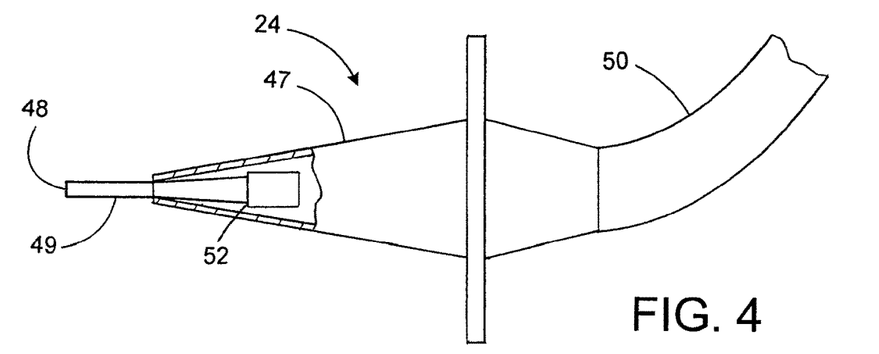
FIG. 4 is a schematic diagram depicting an exemplary catheter tip of a catheter for use as part of the intrathecal delivery system of FIG. 1.

As referenced above, the catheter 18 is in fluid communication with the pump system 14, and particularly the reservoir 32. The catheter has a catheter tip 24 that is inserted into the patient's intrathecal space to administer the bolus of the pharmaceutical agent received from the reservoir, delivered by operation of the pump. FIG. 4 is a schematic diagram depicting an exemplary catheter tip 24 of the catheter 18 for use as part of the intrathecal delivery system of FIG. 1. In many respects, the catheter tip 24 is conventional, including a housing 47 and an exit port 48 constituting an end outlet of a thin tube or needle 49 for the release of the pharmaceutical agent into the intrathecal space. In an alternative embodiment, multiple ports may be provided as a plurality of holes that are spaced circumferentially around the front end of the catheter tip housing 47. The catheter tip is connected to the pump system via a catheter tube 50, which would extend down to the pump system 14. The catheter tip 24 further may include an injector 52. The injector 52 acts a nozzle for enhanced control of the administering of the pharmaceutical agent into the intrathecal space as a high-speed bolus.

The intrathecal delivery system described as to FIGS. 1-4 provides enhanced delivery of a pharmaceutical agent by: (1) administering the pharmaceutical agent intrathecally as a high-speed bolus rather than as a slow continuous flow to increase travel distance, and (2) timing the delivery of the bolus with a portion of a biological cycle, and particularly the cardiac cycle, so that a component of the oscillatory CSF flow further increases the travel distance of the pharmaceutical agent and in a direction toward target spinal receptors. Generally, the controller 40 is configured to receive biological cycle information pertaining to a biological cycle (such as from the biological sensor 26 or 26a), and configured, based on the received biological cycle information, to control the pump 30 to deliver a portion of the pharmaceutical agent as a high-speed bolus at a time corresponding to a time determined based on the biological cycle information. The bolus of the pharmaceutical agent is then administered within a patient's intrathecal space.

More specifically, the controller 40 controls the pump 30 to administer the pharmaceutical agent via the catheter 18 as a high-speed bolus. As understood by those of ordinary skill in the art, a "bolus" delivery refers to the administering of the pharmaceutical agent contained in the pump reservoir as a series of single, discrete dosages separated in time (which is in contrast to a continuous delivery in which the pharmaceutical agent is administered at a constant rate over time). In exemplary embodiments, the volume of each bolus may be in the range 10-20 µL. Accordingly, the controller 40 is configured to cause the pump 30 to administer the pharmaceutical agent in bolus dosages in any suitable requisite bolus volume.

In addition, as used herein, a "high-speed" bolus is a bolus that is administered at a flow rate substantially above conventional constant delivery flow rates (as referenced above, constant delivery flow rates tend to be up to a maximum of about 10 µL/minute). In exemplary embodiments, each bolus is administered at a flow rate of about 10-100 µL/second, or more up to approximately 1 ml per second, until the entire bolus is delivered. The delivery rate of the bolus is controlled utilizing the injector 52 in the catheter tip 18. The injector 52 may be configured as an active nozzle, which is actively controlled by the controller 40 by an electronic connection (wired lead through catheter or wirelessly) to administer the bolus at the desired flow rate. Alternatively, the injector 52 may be configured as a passive nozzle, which passively restricts the flow pathway of the pharmaceutical agent, thereby increasing the flow rate to the desired flow rate under the pressure of the pump. The delivery of the high-speed bolus causes the pharmaceutical agent to spread outward from the catheter tip for a distance significantly father than the travel distance achieved by the constant slow rate of conventional delivery systems.

The delivery of the bolus further may be timed in accordance with a biological cycle, based on biological cycle information obtained by the biological sensor 26 (or 26a). In exemplary embodiments, the biological sensor senses the cardiac cycle. The cardiac cycle may be sensed by directly sensing heart activity, such as by utilizing an electrocardiogram sensor. The cardiac cycle also may be sensed by sensing blood pressure as the blood pressure cycles between systolic and diastolic pressure in correspondence with the heart activity. In exemplary embodiments, the biological sensor additionally may sense the respiratory cycle of expiration and inhalation.

Biological cycle information may be transmitted from the biological sensor 26 via the signal transmitter 29 to the controller 40 of the pump system via the signal receiver 46. Alternatively, when utilizing the integrated biological sensor 26a, the controller 40 receives or reads out the biological cycle information directly from the sensor. The controller 40 then utilizes the biological cycle information to control the administering of the bolus of the pharmaceutical agent. The control operation may depend upon a variety of parameters pertaining to a condition being treated, including, for example, the placement of the catheter and the location of the target spinal receptors along the spinal cord. The various parameters may be entered into the intrathecal delivery application 44, such that when executed by the controller 40, a timing of the bolus delivery is optimized.

For example, as referenced above the CSF tends to flow away from the brain during systole, and toward the brain during diastole. Accordingly, if the target spinal receptors lie between the catheter placement and the brain, the controller operates to administer the bolus during diastole when the CSF flow would tend to deliver the pharmaceutical agent toward the target receptors. Conversely, to similarly account for CSF flow, if the catheter lies between the brain and the target spinal receptors, the controller operates to administer the bolus during systole when the CSF flow is away from the brain. Similar control may be based additionally on the respiratory cycle to take advantage of CSF flow during expiration versus inhalation. For example, a timed release during combined diastole/expiration provides an enhanced travel distance in a direction toward the brain, whereas a timed release during combined systole/inhalation provides an enhanced travel distance in a direction away from the brain.

The result of such control is the enhanced intrathecal delivery of the pharmaceutical agent. First, the travel distance of the pharmaceutical agent from the catheter is increased by administering the pharmaceutical agent as a high-speed bolus that rapidly spreads from the catheter tip. Second, the travel distance of the pharmaceutical agent further is increased by timing the bolus delivery to be commensurate with the CSF flow, which also ensures enhanced flow from the catheter tip in the specific direction of the target spinal receptors. As a result, the pharmaceutical agent is delivered more effectively to the target spinal receptors, without the adverse effects associated with buildup of the pharmaceutical agent adjacent the catheter, including granulomas. Because of such enhanced delivery efficiency, less dosage or concentration of the pharmaceutical agent may be utilized as compared to conventional intrathecal delivery systems.

Figure 5:
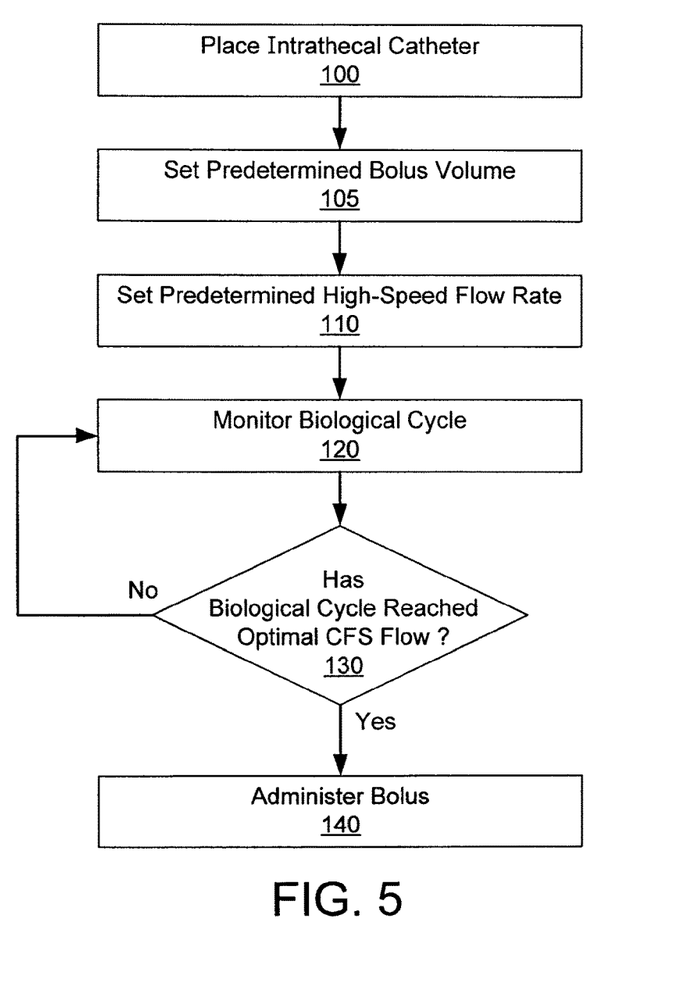
FIG. 5 is a flow chart diagram depicting an overview of an exemplary method of intrathecal delivery of a pharmaceutical agent.

In accordance with the above description, FIG. 5 is a flow chart diagram depicting an overview of an exemplary method of intrathecal delivery of a pharmaceutical agent. Although the exemplary method is described as a specific order of executing functional logic steps, the order of executing the steps may be changed relative to the order described. Also, two or more steps described in succession may be executed concurrently or with partial concurrence. It is understood that all such variations are within the scope of the present invention. In considering the method of FIG. 5, it is presumed that placement of the delivery system, including filling the pump with the pharmaceutical agent, already has been performed. In exemplary embodiments, the method may be performed by the controller 40 executing the delivery application 44 based on biological cycle information detected by the biological sensor 26 or 26a.

Referring to FIG. 5, the method may begin at step 100, at which the catheter is placed at an intrathecal spinal location selected for treating a present medical condition. At step 105, a predetermined volume of a bolus dosage of the pharmaceutical agent is set. At step 110, a predetermined, high-speed flow rate for administering the bolus dosage is set. These parameters may be entered commensurately with a condition being treated, as part of the delivery application 44 to be executed by the controller 40. At step 120, a biological cycle (and preferably the cardiac cycle, by itself or in combination with the respiratory cycle) is monitored by a biological sensor. At step 130, a determination is made as to whether the biological cycle has reached a portion in which CSF flow is optimal for the delivery of the pharmaceutical agent. If a "No" determination is made in step 130, the biological sensor will continue to monitor the biological cycle. If a "Yes" determination is made in step 130, meaning the biological cycle has reached a portion in which CSF flow is optimal for the delivery of the pharmaceutical agent, the method proceeds to step 140.

At step 140, the bolus dosage of the predetermined volume is administered at the predetermined, high-speed flow rate. As described above, the controller 40, as part of the execution of the delivery application 44, may cause the pump 30 to pump the bolus dosage through the catheter 18 to the injector 52. The injector 52 then acts as a control nozzle to administer the bolus intrathecally at the high-speed flow rate, as timed based on the biological cycle information.

In applying the method of FIG. 5, the timing of administering the high-speed bolus may depend on the biological cycle being monitored, and whether a desired flow of the pharmaceutical agent from the catheter tip will be toward the brain or away from the brain, which will depend upon the oscillatory CSF flow. For example, when the biological cycle is the cardiac cycle, the pharmaceutical agent is administered at a time corresponding to a portion of the cardiac cycle. To achieve a desired flow toward the brain, a delivery during diastole may be performed, and conversely to achieve a desired flow away from the brain, a delivery during systole may be performed. When the biological cycle further includes the respiratory cycle, the pharmaceutical agent is administered at a time corresponding to a combined portion of the cardiac cycle and the respiratory cycle. For example, to achieve a desired flow toward the brain, a delivery during diastole/expiration may be performed, and conversely to achieve a desired flow away from the brain, a delivery during systole/inhalation may be performed.

The above descriptions of systems and methods for intrathecal delivery are not limited to the treatment of any particular medical condition. Indeed, such systems and methods generally may be employed as to any medical condition for which intrathecal delivery of a pharmaceutical agent is suitable. Examples of medical conditions appropriate for treatment by the described invention include chronic high blood pressure (also known as chronic or "refractory" hypertension), and chronic pain and spasticity management.

Figure 6:
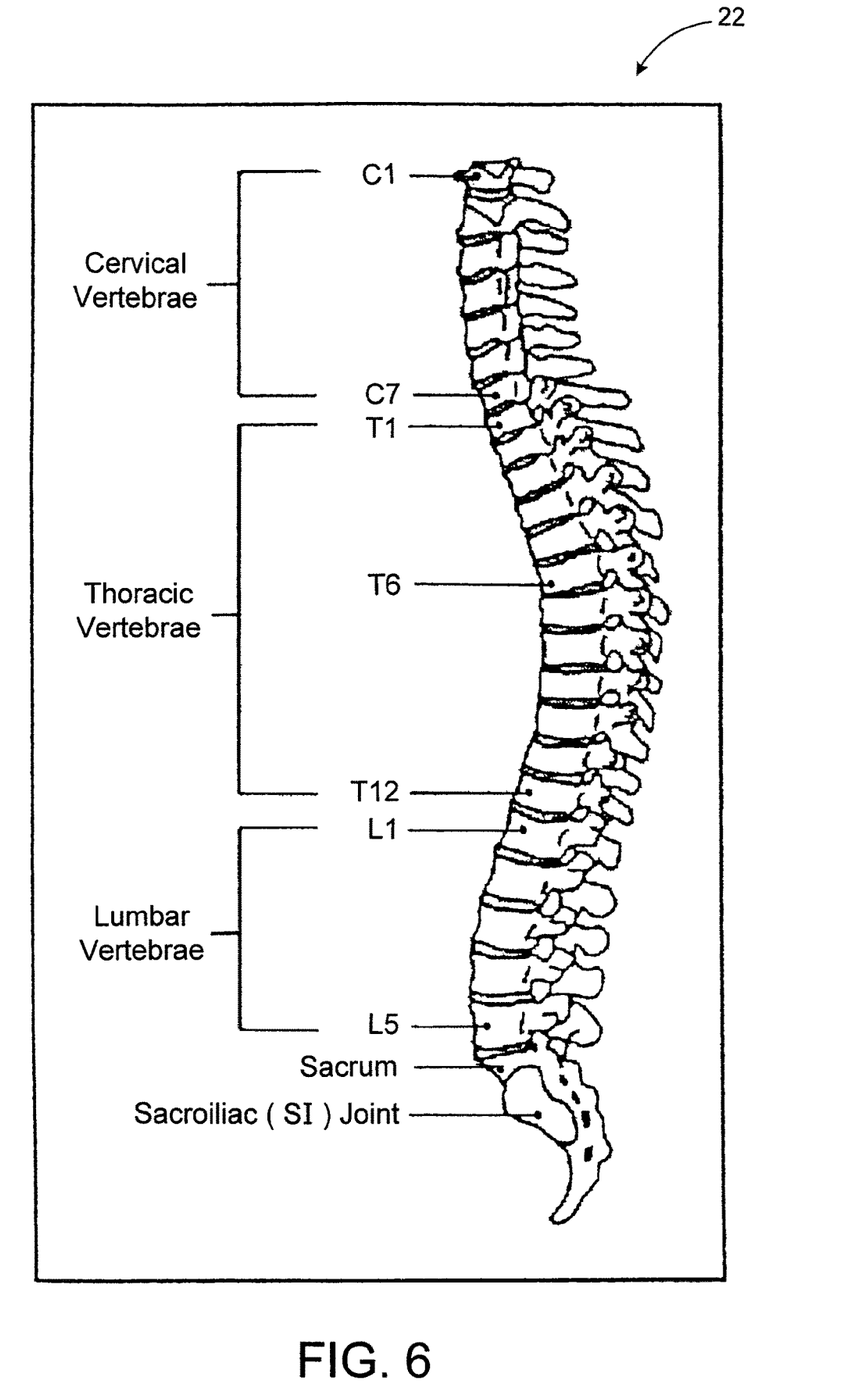
FIG. 6 is a schematic diagram depicting spine configuration.

As background in connection with the treatment of such conditions, FIG. 6 is a schematic diagram depicting spine configuration. The spine 22 is designated as divided into the three regions as depicted in FIG. 6: the cervical region, thoracic region, and lumbar region. Each region is defined by the respective vertebrae within such regions, the vertebrae being numbered sequentially from the top down. Thus, the spine regions correspond to the vertebrae are as follows: cervical region—C1-C7; thoracic region—T1-T12; lumbar region—L1-L5, with the spine ending in the sacrum.

As referred to in the art, the sympathetic nervous system is part of the autonomic nervous system (the portion of the nervous system which controls involuntary bodily functions) specifically associated with the "flight-or-fight" response. Such response is a survival mechanism that permits bodily reaction to danger, as an organism would be in position to either "flight" or "fight" for survival. Both blood pressure and pain sensation, as being associated with such survival mechanism, are controlled in large part by the operation of the sympathetic nervous system. Referring to the spine diagram of FIG. 6, sympathetic control generally is performed by spinal nerves located at the vertebrae range T1-L2.

It has been found that intrathecal delivery of medical conditions associated with sympathetic nervous control is optimal when the catheter is placed within the thoracic region. Precise placement of the catheter, however, will depend upon the locations of the specific spinal nerves or receptors associated with the condition being treated.

The control of blood pressure specifically is affected by spinal nerves located at the vertebrae range T1-T5, which is where the "cardiac accelerator" nerves are located. Refractory hypertension refers to chronic hypertension or high blood pressure (typically 140/90 mmHg for most adults; 130/80 mmHg for high-risk persons such as diabetics) that generally cannot be controlled by conventional oral medications. For such patients, intrathecal delivery of a pharmaceutical agent for controlling blood pressure can be an effective treatment.

In accordance with embodiments of the present invention, a pharmaceutical agent for control of blood pressure is administered intrathecally as a high-speed bolus and timed to at least the cardiac cycle, and in certain embodiments additionally the respiratory cycle. The pharmaceutical agent may include bupivacaine. Bupivacaine is a local anesthetic, which the inventor has found to have a beneficial side effect in treating refractory hypertension. Indeed, bupivacaine has been found to have substantial efficacy in lowering blood pressure. It is known that blood pressure principally is a function of two biological parameters: vascular resistance and cardiac output. Cardiac output in turn is based on heart rate and heart stroke volume. Bupivacaine reduces blood pressure by acting on both parameters associated with blood pressure, by reducing both vascular resistance and heart rate. Bupivacaine also tends not to experience receptor "down regulation", a circumstance by which a higher and higher dosage of a pharmaceutical agent becomes necessary for achieving a comparable benefit. Bupivacaine may be administered either by itself, or in combination with other blood pressure medications such as beta blockers or diuretics.

As referenced above, control of blood pressure is associated with the cardiac accelerator nerves at the T1-T5 vertebrae. Accordingly, intrathecal catheter placement is optimized to deliver bupivacaine to the T1-T5 region, taking into account the increased travel distance provided by the present invention. For example, the catheter may be placed at an intrathecal location corresponding to the T6 location such that the bolus dosage of the pharmaceutical agent (of the predetermined volume at the predetermined flow rate) travels in the intrathecal space to a spinal region including at least a portion of the T1-T5 vertebrae. In this manner, bupivacaine is administered as a high-speed bolus with a timed release during diastole when the CSF is moving toward the brain. If the respiratory cycle additionally is sensed, a timed diastole/expiration release may be employed to further enhance travel distance toward the brain. Such release results in delivery of the bupivacaine to the T1-T5 region from the catheter placement at the T6 vertebra.

In exemplary embodiments, blood pressure control may be performed utilizing a feedback control algorithm. Referring again to FIGS. 1 and 2, as referenced above biological sensors 26 or 26a may be employed to detect cardiac cycle information to time the release of the pharmaceutical agent. Such sensors also may be employed to detect blood pressure, or a separate blood pressure sensor, such as a cuff/monitoring device 25 (see FIG. 1) may be employed. In this context, references to sensing blood pressure may include sensing any one or combination of systolic pressure, diastolic pressure, and/or mean arterial pressure (MAP), which is calculated as a function of the systolic and diastolic pressures.

When the biological sensor detects that blood pressure has risen into an undesirable range, or in other words a high-pressure condition is detected, the intrathecal delivery system for delivering the pharmaceutical agent is triggered such that a bolus of the pharmaceutical agent is administered timed to the cardiac cycle. An undesirable high blood pressure condition may be preset by an operator, and be based on a preset numerical value of diastolic pressure, systolic pressure, and/or MAP, or a preset percentage deviation (e.g., 20%, 30%, etc.) above a blood pressure value designated as "normal". In such embodiment, therefore, the biological sensor has two functions: (1) detecting blood pressure so as to trigger the intrathecal delivery system when the blood pressure becomes high; and (2) monitoring the cardiac cycle (which also may be based on blood pressure detection) to time the actual release of the pharmaceutical agent. The system also may have a "feed forward" component that can account for potential over-correcting of a high blood pressure condition. Such a feed-forward mechanism would ensure that blood pressure settles into a normal range to avoid a low blood pressure condition due to over-correction.

Figure 7:
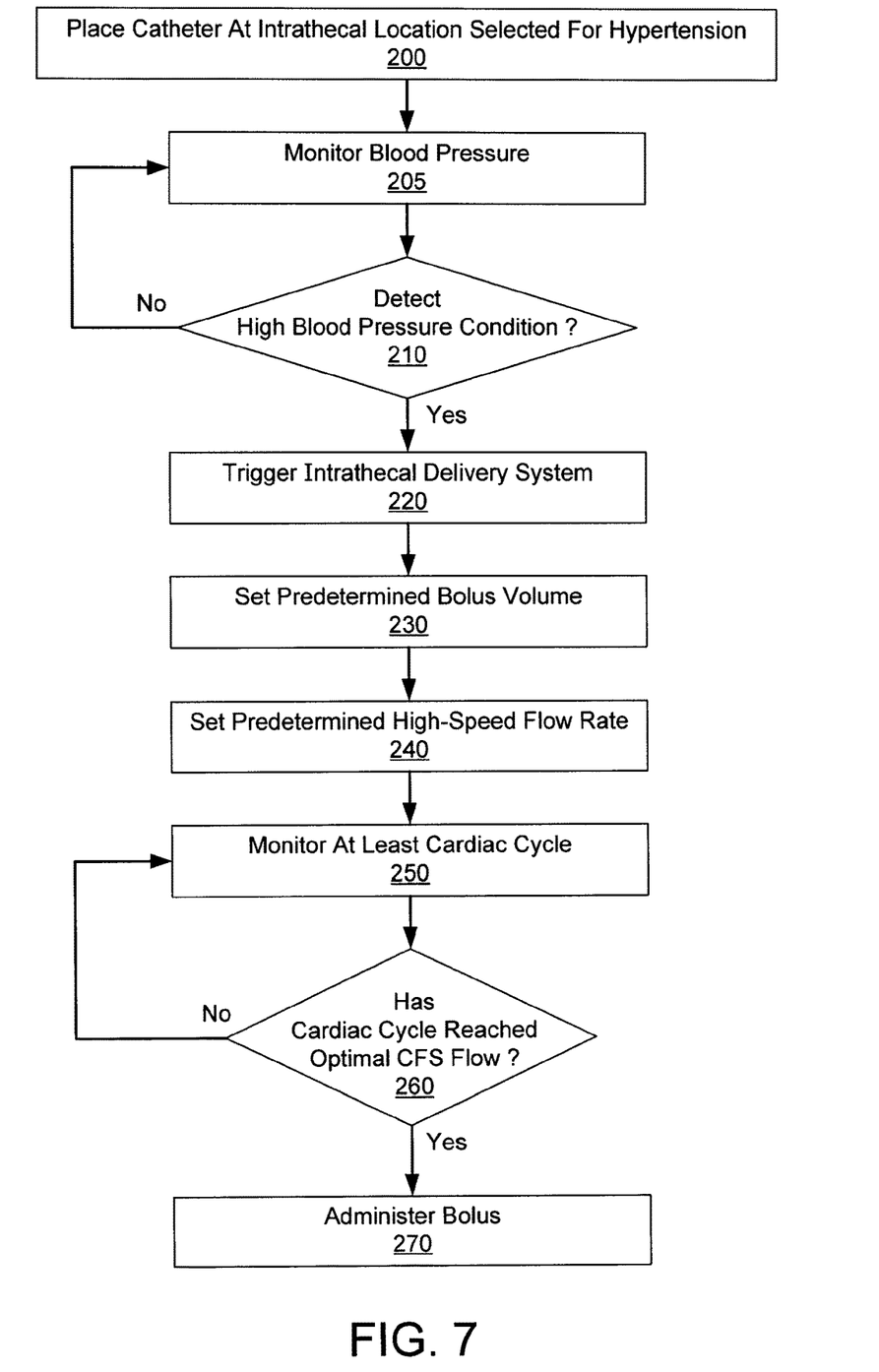
FIG. 7 is a flow chart diagram depicting an overview of an exemplary method of treatment of refractory hypertension by intrathecal delivery of a pharmaceutical agent.

In accordance with the above description, FIG. 7 is a flow chart diagram depicting an overview of an exemplary method of treatment of refractory hypertension by intrathecal delivery of a pharmaceutical agent. Although the exemplary method is described as a specific order of executing functional logic steps, the order of executing the steps may be changed relative to the order described. Also, two or more steps described in succession may be executed concurrently or with partial concurrence. It is understood that all such variations are within the scope of the present invention. In considering the method of FIG. 7, it is presumed that placement of the delivery system, including filling the pump with the pharmaceutical agent for treating high blood pressure, already has been performed. In exemplary embodiments, the method may be performed by the controller 40 executing the delivery application 44 based on biological cycle information detected by the biological sensor 26/26a.

The method may begin at step 200, at which the catheter is placed at a spinal location selected for treating refractory hypertension. For the treatment of refractory hypertension, the catheter may be located at the T6 location for delivery of the pharmaceutical agent to the T1-T5 region. At step 205, blood pressure is monitored by the biological sensor. As referenced above, blood pressure monitoring may include detecting any one or combination of systolic pressure, diastolic pressure, and/or MAP. At step 210, a determination is made as to whether blood pressure has risen into an undesirable range, i.e., a high blood pressure condition is detected based on any suitable predefined criteria. If a "No" determination is made in step 210, the biological sensor will continue to monitor blood pressure. If a "Yes" determination is made in step 210, meaning that a high blood pressure condition is present, the method proceeds to step 220 at which operation of the intrathecal delivery system is triggered.

At this point, the method of FIG. 7 may proceed similarly to that of FIG. 5. At step 230, a predetermined volume of a bolus dosage of the pharmaceutical agent is set. The pharmaceutical agent may include bupivacaine. At step 240, a predetermined, high-speed flow rate for administering the bolus dosage is set. At step 250, at least the cardiac cycle is monitored by a biological sensor. At step 260, a determination is made as to whether the cardiac cycle has reached a portion in which CSF flow is optimal for the delivery of the pharmaceutical agent. In this case, with the catheter placed at the T6 vertebra, the biological sensor is detecting whether the diastolic phase of the cardiac cycle has been reached. If a "No" determination is made in step 260, the biological sensor will continue to monitor the cardiac cycle. If a "Yes" determination is made in step 260, meaning the cardiac cycle has reached a portion in which CSF flow is optimal for the delivery of the pharmaceutical agent (i.e., diastole in this case), the method proceeds to step 270. Alternatively, respiration also may be monitored, and the method may proceed to step 270 when a combined diastole/expiration condition is detected.

At step 270, the bolus dosage of the predetermined volume is administered at the predetermined, high-speed flow rate. As described above (see FIGS. 1-4), the controller 40, as part of the execution of the delivery application 44, may cause the pump 30 to pump the bolus dosage through the catheter 18 to the injector 52. The injector 52 then acts as a control nozzle to administer the bolus intrathecally at the high-speed flow rate, as time based on the cardiac cycle (and perhaps additional respiratory cycle) information.

The methods of FIGS. 5 and 7 may be adapted to configure the intrathecal delivery system for the treatment of any suitable condition. As another example, as referenced above, intrathecal delivery also may be suitable for the treatment of chronic pain with or without spasticity (referred to going forward simply as "chronic pain"). Common pharmaceutical agents delivered intrathecally to treat chronic pain include morphine and hydromorphone compounds.

The spinal receptors for pain generally are located at the T10-T12 spinal region. Accordingly, intrathecal catheter placement is optimized to deliver pain medication to the T10-T12 region, taking into account the increased travel distance provided by the present invention. For example, the catheter may be placed at the L1 vertebra location. Pain medication may then be administered as a high-speed bolus with a timed release during diastole or diastole/expiration when the CSF is moving toward the brain. Such release results in effective delivery of the pain medication, which travels from the L1 catheter location to a spinal region including at least a portion of the T10-T12 vertebrae. Conversely, the catheter may be placed at the T9 location. Pain medication may then be administered as a high-speed bolus with a timed release during systole or systole/inhalation when the CSF is moving away from the brain. Such release results in delivery of the pain medication from the T9 catheter location to a spine region including at least a portion of the T10-T12 vertebrae.

Chronic pain, in contrast to blood pressure, is not an ordinary biological cycle that would be detectable with a sensor. Accordingly, the trigger for the intrathecal delivery system for treating chronic pain would differ from the trigger for treating refractory hypertension. In one embodiment, the intrathecal delivery system for pain management would simply be triggered periodically and automatically at preset times or periodic intervals. Such trigger times may be inputted into the delivery application 44 specifically associated with the treatment of chronic pain. In another embodiment, there may be a manual input device, such as a button on the delivery system, that would permit a patient to trigger the delivery system manually when the patient feels pain. Once triggered, the pain medication may then be administered as a high-speed bolus with a timed release when the CSF is moving toward the T10-T12 region relative to the catheter position.

The present invention has been described principally with respect to an intrathecal delivery system. Comparable systems and methods to those described above may be employed to deliver a pharmaceutical agent into other internal fluid-filled bodily spaces or cavities. Additional bodily cavities may include, for example, interstitial or venous cavities. A high speed bolus may be employed for delivery of a pharmaceutical agent into such bodily cavities, or any other suitable bodily cavities. In addition, to the extent fluid flow within such cavities is tied to or influenced by a biological cycle, the delivery of the pharmaceutical agent further may be timed in accordance with biological cycle information so as to enhance deliver of the pharmaceutical agent to a specific location within or adjacent to the bodily cavity or space.

In accordance with the above description, and aspect of the invention is an intrathecal delivery system for intrathecal delivery of a pharmaceutical agent. In exemplary embodiments, the intrathecal delivery system includes a reservoir containing a volume of the pharmaceutical agent, a pump configured to deliver a portion of the pharmaceutical agent contained in the reservoir, and a controller. The controller is configured to receive biological cycle information pertaining to a biological cycle, and configured, based on the received biological cycle information, to control the pump to deliver the portion of the pharmaceutical agent as a high-speed bolus at a time corresponding to a time determined based on the biological cycle information, wherein the bolus of the pharmaceutical agent is administered within a patient's intrathecal space.

In an exemplary embodiment of the intrathecal delivery system, wherein the high-speed bolus corresponds to a delivery rate of the bolus of at least 10 µL per second.

In an exemplary embodiment of the intrathecal delivery system, the high-speed bolus corresponds to a delivery rate of the bolus within a range of 10-100 µL per second.

In an exemplary embodiment of the intrathecal delivery system, a volume of the high-speed bolus is within a range of 10-20 µL.

In an exemplary embodiment of the intrathecal delivery system, the system further includes a biological sensor that senses the biological cycle information and transmits the biological cycle information to the controller.

In an exemplary embodiment of the intrathecal delivery system, the biological cycle comprises a cardiac cycle, and the controller is configured to control the pump to deliver the portion of the pharmaceutical agent at a time corresponding to a portion of the cardiac cycle.

In an exemplary embodiment of the intrathecal delivery system, the biological cycle further comprises a respiratory cycle, and the controller is configured to control the pump to deliver the portion of the pharmaceutical agent at a time corresponding to a combined portion of the cardiac cycle and the respiratory cycle.

In an exemplary embodiment of the intrathecal delivery system, the controller is configured to control the pump to deliver the portion of the pharmaceutical agent at a time corresponding to one of diastole/expiration or systole/inhalation as the combined portion of the cardiac cycle and the respiratory cycle.

In an exemplary embodiment of the intrathecal delivery system, the system further includes a catheter in fluid communication with the reservoir, wherein the catheter has a catheter tip that is inserted into the patient's intrathecal space to administer the bolus of the pharmaceutical agent received from the reservoir delivered by operation of the pump.

In an exemplary embodiment of the intrathecal delivery system, the catheter tip comprises an injector to control a flow rate of the high speed bolus into the patient's intrathecal space.

Another aspect of the invention is a method of intrathecal delivery of a pharmaceutical agent in a patient's intrathecal space. In exemplary embodiments of method of intrathecal delivery includes the steps of: placing a catheter at an intrathecal spine location selected for treating a present medical condition; setting a predetermined volume of a bolus dosage of the pharmaceutical agent; setting a predetermined high-speed flow rate for administering the bolus dosage of the pharmaceutical agent; monitoring a biological cycle; determining whether the biological cycle has reached a portion in which a cerebrospinal fluid (CSF) flow is optimal for intrathecal delivery of the pharmaceutical agent; and when the biological cycle has reached a portion in which the CSF flow is optimal for intrathecal delivery of the pharmaceutical agent, administering the bolus dosage of the pharmaceutical agent of the predetermined volume at the predetermined flow rate into the patient's intrathecal space.

In an exemplary embodiment of the method of intrathecal delivery, the predetermined high-speed flow rate corresponds to a delivery rate of the bolus of at least 10 µL per second.

In an exemplary embodiment of the method of intrathecal delivery, the predetermined high-speed flow rate corresponds to a delivery rate of the bolus within a range of 10-100 µL per second.

In an exemplary embodiment of the method of intrathecal delivery, the predetermined volume of the high-speed bolus is within a range of 10-20 µL.

In an exemplary embodiment of the method of intrathecal delivery, the biological cycle comprises a cardiac cycle, and the pharmaceutical agent is administered at a time corresponding to a portion of the cardiac cycle.

In an exemplary embodiment of the method of intrathecal delivery, the biological cycle further comprises a respiratory cycle, and the pharmaceutical agent is administered at a time corresponding to a combined portion of the cardiac cycle and the respiratory cycle.

In an exemplary embodiment of the method of intrathecal delivery, the pharmaceutical agent is administered at a time corresponding to one of diastole/expiration or systole/inhalation as the combined portion of the cardiac cycle and the respiratory cycle.

In an exemplary embodiment of the method of intrathecal delivery, the present medical condition is refractory hypertension, and the method further includes the steps of: placing the catheter at an intrathecal spine location corresponding to the T6 vertebra; monitoring at least a cardiac cycle as the biological cycle; determining whether the cardiac cycle has reached diastole; and when the cardiac cycle has reached diastole, administering the bolus dosage of the pharmaceutical agent of the predetermined volume at the predetermined flow rate into the patient's intrathecal space, wherein the pharmaceutical agent travels in the intrathecal space to a spinal region comprising at least a portion of the T1-T5 vertebrae.

In an exemplary embodiment of the method of intrathecal delivery, the method further includes: further monitoring the respiratory cycle as part of monitoring the biological cycle; determining whether the respiratory cycle has reached expiration; and when a combined cardiac cycle/respiratory cycle reaches diastole/expiration, administering the pharmaceutical agent.

In an exemplary embodiment of the method of intrathecal delivery, the pharmaceutical agent includes bupivacaine.

In an exemplary embodiment of the method of intrathecal delivery, the method further includes monitoring blood pressure; determining whether the blood pressure has risen to a high blood pressure condition; and when the blood pressure has risen to a high blood pressure condition, triggering an intrathecal delivery system for delivering the pharmaceutical agent, wherein once triggered, the intrathecal delivery system performs the steps recited in claim 18.

In an exemplary embodiment of the method of intrathecal delivery, the method further includes: controlling the intrathecal delivery system to perform feed forward control to account for potential over-correction of the high blood pressure condition.

In an exemplary embodiment of the method of intrathecal delivery, the present medical condition is chronic pain with or without spasticity, and the method further includes the steps of: placing the catheter at an intrathecal spine location corresponding to the L1 vertebra; monitoring at least a cardiac cycle as the biological cycle; determining whether the cardiac cycle has reached diastole; and when the cardiac cycle has diastole, administering the bolus dosage of the pharmaceutical agent of the predetermined volume at the predetermined flow rate into the patient's intrathecal space, wherein the pharmaceutical agent travels in the intrathecal space to a spinal region comprising at least a portion of the T10-T12 vertebrae.

In an exemplary embodiment of the method of intrathecal delivery, the method further includes: further monitoring the respiratory cycle as part of monitoring the biological cycle; determining whether the respiratory cycle has reached expiration; and when a combined cardiac cycle/respiratory cycle reaches diastole/expiration, administering the pharmaceutical agent.

In an exemplary embodiment of the method of intrathecal delivery, the pharmaceutical agent includes at least one of morphine or a hydromorphone compound.

Another aspect of the invention is a delivery system for delivery of a pharmaceutical agent into a fluid-filled bodily cavity. In exemplary embodiments, the delivery system includes a reservoir containing a volume of the pharmaceutical agent, a pump configured to deliver a portion of the pharmaceutical agent contained in the reservoir, and a controller. The controller is configured to receive biological cycle information pertaining to a biological cycle, and configured, based on the received biological cycle information, to control the pump to deliver the portion of the pharmaceutical agent as a high-speed bolus at a time corresponding to a time determined based on the biological cycle information, wherein the bolus of the pharmaceutical agent is administered within the bodily cavity.

In an exemplary embodiment of the delivery system, the bodily cavity is one of an intrathecal space, a venous space, or an interstitial space.

Another aspect of the invention is a method of delivery of a pharmaceutical agent into a fluid-filled bodily cavity. In exemplary embodiments, method of delivery includes the steps of: placing a catheter at a location within the bodily cavity selected for treating a present medical condition; setting a predetermined volume of a bolus dosage of the pharmaceutical agent; setting a predetermined high-speed flow rate for administering the bolus dosage of the pharmaceutical agent; monitoring a biological cycle; determining whether the biological cycle has reached a portion in which a) flow of fluid within the bodily cavity is optimal for delivery of the pharmaceutical agent; and when the biological cycle has reached a portion in which the fluid flow is optimal for delivery of the pharmaceutical agent, administering the bolus dosage of the pharmaceutical agent of the predetermined volume at the predetermined flow rate into the bodily cavity.

In an exemplary embodiment of the method of delivery, the bodily cavity is one of an intrathecal space, a venous space, or an interstitial space.

Although certain embodiments have been shown and described, it is understood that equivalents and modifications falling within the scope of the appended claims will occur to others who are skilled in the art upon the reading and understanding of this specification.

What is claimed is:

1. An intrathecal delivery system for intrathecal delivery of a pharmaceutical agent comprising:
   a reservoir containing a volume of the pharmaceutical agent;
   a pump configured to deliver a portion of the pharmaceutical agent contained in the reservoir; and
   a controller configured to receive biological cycle information pertaining to a biological cycle, and configured, based on the received biological cycle information, to control the pump to deliver the portion of the pharmaceutical agent as a high-speed bolus;
   wherein the bolus of the pharmaceutical agent is administered within a patient's intrathecal space; and
   wherein controller further is configured to:
   determine based on the biological cycle information whether the biological cycle has reached a portion in which a cerebrospinal fluid (CSF) flow is optimal for intrathecal delivery of the pharmaceutical agent; and
   when the biological cycle has reached a portion in which the CSF flow is optimal for intrathecal delivery of the pharmaceutical agent, control the pump to administer the bolus of the pharmaceutical agent into the patient's intrathecal space, and the optimal CSF flow is when the CSF flow favors travel of the pharmaceutical agent in a direction toward target spinal receptors to increase a distance of travel of the pharmaceutical agent.

2. The intrathecal delivery system of claim 1, further comprising a biological sensor that senses the biological cycle information and transmits the biological cycle information to the controller.

3. The intrathecal delivery system of claim 2, wherein the biological cycle comprises a cardiac cycle, and the controller is configured to control the pump to deliver the portion of the pharmaceutical agent at a time corresponding to a portion of the cardiac cycle.

4. The intrathecal delivery system of claim 3, wherein the biological cycle further comprises a respiratory cycle, and the controller is configured to control the pump to deliver the portion of the pharmaceutical agent at a time corresponding to a combined portion of the cardiac cycle and the respiratory cycle.

5. The intrathecal delivery system of claim 1, further comprising a catheter in fluid communication with the reservoir, wherein the catheter has a catheter tip that is inserted into the patient's intrathecal space to administer the bolus of the pharmaceutical agent received from the reservoir delivered by operation of the pump.

6. A method of intrathecal delivery of a pharmaceutical agent in a patient's intrathecal space comprising the steps of:
    placing a catheter at an intrathecal spine location selected for treating a present medical condition;
    setting a predetermined volume of a bolus dosage of the pharmaceutical agent;
    setting a predetermined high-speed flow rate for administering the bolus dosage of the pharmaceutical agent;
    monitoring a biological cycle;
    determining whether the biological cycle has reached a portion in which a cerebrospinal fluid (CSF) flow is optimal for intrathecal delivery of the pharmaceutical agent; and
    when the biological cycle has reached a portion in which the CSF flow is optimal for intrathecal delivery of the pharmaceutical agent, administering the bolus dosage of the pharmaceutical agent of the predetermined volume at the predetermined flow rate into the patient's intrathecal space, and the optimal CSF flow is when the CSF flow favors travel of the pharmaceutical agent in a direction toward target spinal receptors to increase a distance of travel of the pharmaceutical agent.

7. The method of intrathecal delivery of claim 6, wherein the predetermined high-speed flow rate corresponds to a delivery rate of the bolus of at least 10 µL per second.

8. The method of intrathecal delivery of claim 7, wherein the predetermined high-speed flow rate corresponds to a delivery rate of the bolus within a range of 10-100 µL per second.

9. The method of intrathecal delivery of claim 8, wherein the predetermined volume of the high-speed bolus is within a range of 10-20 µL.

10. The method of intrathecal delivery of claim 6, wherein the biological cycle comprises a cardiac cycle, and the pharmaceutical agent is administered at a time corresponding to a portion of the cardiac cycle.

11. The method of intrathecal delivery of claim 10, wherein the biological cycle further comprises a respiratory cycle, and the pharmaceutical agent is administered at a time corresponding to a combined portion of the cardiac cycle and the respiratory cycle.

12. The method of intrathecal delivery of claim 11, wherein the pharmaceutical agent is administered at a time corresponding to one of diastole/expiration or systole/inhalation as the combined portion of the cardiac cycle and the respiratory cycle.

13. The method of intrathecal delivery of claim 6, wherein the present medical condition is refractory hypertension, the method further comprising the steps of:
    placing the catheter at an intrathecal spine location corresponding to the T6 vertebra;
    monitoring at least a cardiac cycle as the biological cycle;
    determining whether the cardiac cycle has reached diastole; and
    when the cardiac cycle has reached diastole, administering the bolus dosage of the pharmaceutical agent of the predetermined volume at the predetermined flow rate into the patient's intrathecal space, wherein the pharmaceutical agent travels in the intrathecal space to a spinal region comprising at least a portion of the T1-T5 vertebrae.

14. The method of intrathecal delivery of claim 13, further comprising:
    further monitoring the respiratory cycle as part of monitoring the biological cycle;
    determining whether the respiratory cycle has reached expiration; and
    when a combined cardiac cycle/respiratory cycle reaches diastole/expiration, administering the pharmaceutical agent.

15. The method of intrathecal delivery of claim 13, wherein the pharmaceutical agent includes bupivacaine.

16. The method of intrathecal delivery of claim 13, further comprising:
    monitoring blood pressure;
    determining whether the blood pressure has risen to a high blood pressure condition; and
    when the blood pressure has risen to a high blood pressure condition, triggering an intrathecal delivery system for delivering the pharmaceutical agent.

17. The method of intrathecal delivery of claim 16, further comprising:
    controlling the intrathecal delivery system to perform feed forward control to account for potential over-correction of the high blood pressure condition.

18. The method of intrathecal delivery of claim 6, wherein the present medical condition is chronic pain with or without spasticity, the method further comprising the steps of:
    placing the catheter at an intrathecal spine location corresponding to the L1 vertebra;
    monitoring at least a cardiac cycle as the biological cycle;
    determining whether the cardiac cycle has reached diastole; and
    when the cardiac cycle has diastole, administering the bolus dosage of the pharmaceutical agent of the predetermined volume at the predetermined flow rate into the patient's intrathecal space, wherein the pharmaceutical agent travels in the intrathecal space to a spinal region comprising at least a portion of the T10-T12 vertebrae.

19. The method of intrathecal delivery of claim 18, further comprising:
    further monitoring the respiratory cycle as part of monitoring the biological cycle;
    determining whether the respiratory cycle has reached expiration; and
    when a combined cardiac cycle/respiratory cycle reaches diastole/expiration, administering the pharmaceutical agent.

20. The method of intrathecal delivery of claim 19, wherein the pharmaceutical agent includes at least one of morphine or a hydromorphone compound.

* * * * *